(12) United States Patent
Revel et al.

(10) Patent No.: US 8,247,539 B2
(45) Date of Patent: Aug. 21, 2012

(54) PROCESS FOR PREPARING MATERIALS BY GRAFTING HALOGENATED PHOSPHORUS-CONTAINING GROUPS ONTO AN INORGANIC SURFACE

(75) Inventors: Renaud Revel, Serpaize (FR); Florence Brodard-Severac, Moisson (FR); Gilles Guerrero, Beziers (FR); Hubert Mutin, Clapiers (FR); Alain Forestiere, Vernaison (FR); Alexandra Chaumonnot, Lyons (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 380 days.

(21) Appl. No.: 12/375,742

(22) PCT Filed: Jul. 6, 2007

(86) PCT No.: PCT/FR2007/001167
§ 371 (c)(1),
(2), (4) Date: Nov. 10, 2009

(87) PCT Pub. No.: WO2008/015322
PCT Pub. Date: Feb. 7, 2008

(65) Prior Publication Data
US 2010/0069618 A1   Mar. 18, 2010

(30) Foreign Application Priority Data
Jul. 31, 2006   (FR) ...................................... 06 07047

(51) Int. Cl.
C23C 22/56 (2006.01)
C07F 9/02 (2006.01)
C07F 5/06 (2006.01)
C07F 7/02 (2006.01)
C07F 5/00 (2006.01)

(52) U.S. Cl. ............ 534/15; 148/274; 148/254; 148/95; 148/250; 148/272; 556/174; 556/13; 556/405; 556/173; 568/8; 502/152

(58) Field of Classification Search ........................ None
See application file for complete search history.

(56) References Cited

U.S. PATENT DOCUMENTS

| 4,788,176 A | 11/1988 | Wieserman et al. |
| 4,994,429 A * | 2/1991 | Wieserman et al. .......... 502/401 |
| 5,059,258 A | 10/1991 | Wefers et al. |
| 2002/0011280 A1 | 1/2002 | Nitowski et al. |
| 2002/0023573 A1 | 2/2002 | Forestiere et al. |
| 2004/0001959 A1 | 1/2004 | Schwartz et al. |

FOREIGN PATENT DOCUMENTS
EP   1 180 396 A1   2/2002
WO   WO 99/66104 A2   12/1999

OTHER PUBLICATIONS
Guerrero et al. Chem. Mater. 2001, 13, 4367-4373.*
Corriu et al. J. Mater. Chem., 1998, 8(8), 1827-1833.*

* cited by examiner

Primary Examiner — Melvin C Mayes
Assistant Examiner — Yun Qian
(74) Attorney, Agent, or Firm — Millen, White, Zelano & Branigan, P.C.

(57) ABSTRACT

The invention concerns a process for preparing a hybrid organic-inorganic material (HOIM) with phosphorus-containing bridges between the surface of an inorganic substrate containing an element M and one or more organic groups of the covalent M-O-P-R type, said process using, as a precursor for said organic group or groups, at least one organophosphorus acid halide with formula $R_xP(O)X_y$ in which x=1 or 2, y=3–x, X being a halogen and R designating at least one organic alkyl, aryl or aryl-alkyl group.

Non-exhaustive applications for the hybrid organic-inorganic material obtained by the process of the invention are in the fields of anti-corrosion, lubrication, microelectronics, nanotechnologies, composite materials, heterogeneous catalysis, supported catalysis, depollution and biomedical applications.

18 Claims, No Drawings

PROCESS FOR PREPARING MATERIALS BY GRAFTING HALOGENATED PHOSPHORUS-CONTAINING GROUPS ONTO AN INORGANIC SURFACE

The present invention relates to a process for preparing a hybrid organic-inorganic material comprising organic groups containing phosphorus bonded via a covalent bond between an inorganic surface and one or more organic fragments. In the process of the invention, elemental phosphorus is introduced into a material containing an element M using organophosphorus acid halides in an anhydrous medium which can bond the organic fragments R to the inorganic surface via M-O-P bonds.

Non-exhaustive applications for the hybrid organic-inorganic material obtained by the process of the invention are in the fields of anti-corrosion, lubrication, microelectronics, nanotechnologies, composite materials, heterogeneous catalysis, supported catalysis, depollution and biomedical applications.

Prior Art

The modification or functionalization of inorganic surfaces by a grafting technique for phosphorus-containing groups is more particularly described in prior art documents which describe the use of phosphoric acids (a, X=OH), phosphinic acids (b, X=OH), or phosphoric acid monoesters (c and c', X=OH) or diesters (d, X=OH).

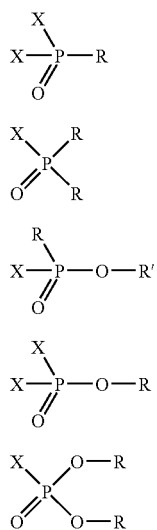

The Aluminum Company of America's patent U.S. Pat. Nos. 4,788,176, 4,786,628, 4,957,890, 4,994,429 describe materials defined by an inorganic surface modified by fragments R which are bonded thereto via the phosphonic, phosphinic or phosphoric groups described above. Fragments R may be either hydrogen or organic chains containing 1 to 30 carbon atoms. In those patents, modification of the surface results in the formation of a monolayer of functional organic groups containing phosphorus.

Further, International patent application WO-A-04072120 also describes a surface modification process for creating a dense monolayer by grafting an organic fragment onto a substrate via a phosphonic acid group.

U.S. Pat. No. 6,645,644 also describes the use of phosphonic or phosphoric acids to cover an inorganic substrate. The substrates mentioned in that patent are generated by depositing a layer of transition metal alkoxides from groups IVB, VB and VIB onto oxide supports or metallic supports with an oxidized surface.

EP-A-1 180 396 also describes functionalized materials comprising organic phosphorus based groups linked to the surface via oxygen atoms. All organic molecules used are of the phosphonate, phosphinate or phosphate type, or they are of the phosphonic, phosphinic or phosphoric acid alkyl ester or silyl ester type.

Surface modification by phosphonic or phosphinic acid esters, alkyl esters or silyl esters is also described in the literature (Guerrero, G; Mutin P H; Vioux A, J Mater Chem 2001, 11, 3161-3165; Guerrero G, Chaplais G, Mutin P H, Le Bideau J, Leclercq D; Vioux A, Mat Res Soc Symp Proc 2001, 628, CC6.6.1-CC6.6.6; Frantz R, Durand J-O, Grainer M, Lanneau G F, Tet Lett 2004, 45, 2935-2937; Villemin D, Moreau B, Simeon F, Maheut G, Fernendez C, Montouillout V, Caignaert V, Jaffres P-A, Chem Comm 2001, 2060-2061; Guerrero G, Mutin P H, Vioux A, Chem Mater 2001, 13, 4367)

Thus, prior art documents describe grafting organophosphorus compounds onto the surface hydroxyls of substrates using processes employing water or alcohol. Subsequent elimination of those elements by heat treatment inexorably leads to the formation in the material of lamellar phosphonate, phosphinate or phosphate type compounds of elements M which are potentially prejudicial to the applications described above. A further disadvantage linked to the use of the organophosphorus precursors cited in the prior art is the limitation on the quantity of organophosphorus grafts on the surface of the substrate by competition with the adsorption of molecules of water or alcohol.

The Applicant has discovered that using phosphonic or phosphinic acid chlorides to prepare a hybrid organic-inorganic material by grafting enjoys unexpected advantages.

In this regard, one of the advantages of the preparation process of the invention is that it avoids the formation of lamellar phases on the surface of the inorganic substrate.

Another advantage of the preparation process of the invention is that it allows a large quantity of organophosphorus compounds to be grafted onto the surface of said substrate, accounting for the improvement in the adsorption selectivity at the surface.

SUMMARY OF THE INVENTION

The invention concerns a process for preparing a hybrid organic-inorganic material (HOIM) with phosphorus-containing bridges between the surface of an inorganic substrate containing an element M and one or more organic groups of the covalent M-O-P-R type, said process using, as a precursor for said organic group or groups, at least one organophosphorus acid halide with formula $R_xP(O)X_y$, in which $x=1$ or $2$, $y=3-x$, X being a halogen and R designating at least one organic alkyl, aryl or aryl-alkyl group.

DETAILED DESCRIPTION OF THE INVENTION

The present invention concerns a process for preparing a hybrid organic-inorganic material (HOIM) with phosphorus-containing bridges between the surface of an inorganic substrate containing an element M and the organic group, said process using organophosphorus acid halides to modify the surface by grafting to bond an organic group R by dint of a M-O-P-R bond.

Said acid halides satisfy the formula $R_xP(O)X_y$ in which $x=1$ or $2$ and $y=3-x$.

X is a halogen element, preferably selected from chlorine and bromine; more preferably, X is chlorine.

R denotes at least one organic alkyl, aryl or aryl-alkyl group, optionally halogenated, saturated or otherwise, branched or otherwise and which may or may not carry one or more functional organic groups. The hydrocarbon chain of the organic group(s) R contains at least one carbon, usually 1 to 30 carbon atoms and more preferably 3 to 18 carbon atoms.

Substitutions of hydrogen on the hydrocarbon chain by halogens, preferably chorine or bromine, more preferably chlorine, may produce completely substituted chains. More preferably, no substitution is carried out.

The organic functional groups are preferably carboxylic acids and their derivatives, amines and their derivatives, sulphonic acids and their derivatives, thiols and their derivatives, or polysulphides and their derivatives. The term "derivatives" means esters and halogens, including polymerizable or polycondensable motifs.

In general, the inorganic substrate has an oxide-containing or hydroxyl-containing surface which will generate an anchor point with the organophosphorus compound.

Preferably, the inorganic substrate is selected from the group constituted by oxides or hydroxides of elements M, with M being selected from groups IB, IIB, IIIB, IVB, VB, VIB, VIIB, VIII, IIIA, IVA, VA, the lanthanides and actinides of the periodic table (Handbook of Chemistry and Physics, $55^{th}$ edition, 1974-75), carbonates of elements from groups IA and IIA, and natural or synthetic minerals.

Said oxides and hydroxides may be simple, i.e. comprising just one element M, or mixed, i.e. comprising several elements M, preferably 2 to 4 elements. They may have either a crystallographic structure defined in the crystallographic sense (zeolites and the like, polymorphic forms of alumina), or no crystallographic structure (for example silica), or a mixture of amorphous and structured phases, or they may be compounds of solid solutions or have an amorphous texture with a uniform and organized porosity, termed a mesostructure.

Preferably, the oxides used are selected from the group constituted by alumina, titanium dioxide, silica, zeolites and mesostructured silica, Highly preferably, the oxide used as an inorganic substrate is titanium dioxide.

The inorganic substrate may also be selected from iron, aluminium, titanium, silicon, copper and alloys such as brass or steels.

The inorganic substrate may also be selected from carbonates of elements from groups IA and IIA. Preferably, calcium carbonate is used.

The inorganic substrate may also be selected from natural or synthetic minerals, preferably from talc, apatite, quartz and gypsum.

The inorganic substrate may also be selected from ceramics such as silicon nitride, semiconductors such as silicon, gallium arsenide, gallium nitride and silicon carbide.

The process for preparing a hybrid organic-inorganic material using organophosphorus acid halides of the present invention comprises the following steps:
 a) pre treating the inorganic substrate, consisting of heating said substrate to a temperature in the range 20° C. to 300° C. at an absolute gas pressure in the range 0.01 Pa to 0.2 MPa and for a period in the range 1 to 20 hours;
 b) bringing the anhydrous organic solution of at least one organophosphorus compound selected from acid halides into contact with said inorganic substrate obtained in step a) to produce covalent M-O-P-R type bonds between the organic and inorganic phases;
 c) filtering and washing the solid obtained in step b);
 d) heat treating the solid obtained in step c) at a temperature in the range 25° C. to 500° C., at an absolute air pressure in the range 0.01 Pa to 0.2 MPa.

The inorganic substrate of the invention undergoes a pre treatment (step a) to reduce the residual water content which would lead to unwanted hydrolysis of the organophosphorus compounds. The term "residual water" means the quantity of water physisorbed on the surface of the inorganic substrate. In general, any drying process which is known to the skilled person (for example in an oven or in a vacuum dryer) which can reduce the water content of the solid may be used. Preferably, the inorganic substrate is pre treated at a temperature in the range 20° C. to 300° C. at an absolute pressure of a gas selected from air, nitrogen and helium or any mixture of these gases, in the range 0.01 to 0.2 MPa for a period in the range 1 to 48 hours. More preferably, the inorganic substrate is pre treated at a temperature in the range 40° C. to 150° C. at an absolute air pressure in the range 1 Pa to 0.1 MPa, preferably in the range 10 to 1000 Pa, for a period in the range 1 to 20 hours, preferably 5 to 18 hours.

In accordance with step b) of the preparation process, the solution used for the organophosphorus compound must be organic and anhydrous. The organic solvents may be alcohols, for example methanol, ethanol or propanol, or any other organic solvent such as dichloromethane, toluene, tetrahydrofuran, acetone or mixtures of these solvents. Preferably, the solvent is toluene. The associated reaction temperatures are in the temperature range from ambient temperature to the boiling point of the solvent selected as a function of the nature of the organic precursor or precursors. To avoid hydrolysis of the organophosphorus compound, the solvent is dehydrated prior to use using techniques which are known to the skilled person. The quantity of residual water in the solvent is less than 5000 ppm, preferably less than 1000 ppm, more preferably less than 300 ppm. The use of such anhydrous organic solvents necessitates operating in an inert atmosphere, for example with helium, nitrogen or argon. Contact of the organophosphorus compound and inorganic substrate in accordance with step b) of the preparation process is carried out with stirring for a period in the range 5 minutes to 30 days, preferably 1 day to 10 days, to ensure the formation of covalent bonds between the organic and inorganic phases. Further, said contact may be carried out in the dark, in the event of using a photosensitive substrate.

In step c) of the preparation process of the invention, a washing step is carried out after the solid has been isolated. For this operation, organic solvents or mixed aqueous-organic solutions may be used. The organic solvents may be alcohols, for example methanol, ethanol or propanol, or any other organic solvent such as dichloromethane, toluene, tetrahydrofuran, acetone or mixtures of those solvents. Preferably, the washing solvents used are toluene, acetone and mixtures of these solvents with deionized water. Several successive washing steps may be carried out to free the hybrid organic-inorganic material from unreacted organophosphorus compounds.

In step d) of the preparation process of the invention, a heat treatment step is carried out on the solid obtained in step c). Said heat treatment step is operated at a temperature in the range 250° C. to 500° C. and at an absolute air pressure in the range 0.01 Pa and 0.2 MPa, preferably at a temperature in the range 50° C. to 150° C. and at a reduced pressure between 10 and 1000 Pa. The heat treatment period is in the range 1 hour to 36 hours, preferably 6 hours to 18 hours.

The organophosphorus hybrid materials produced in the process of the invention have a graft density, represented by a phosphorus surface density, in the range 2 to 10 P atoms/nm$^2$, preferably in the range 2 to 5 P atoms /nm². These materials are free of phosphate, phosphinate or phosphonate phases of elements M, this characteristic being connected to the absence of peaks associated with these phases by $^{31}$P NMR analysis.

The hybrid materials produced using the process of the invention may be characterized by several analytical techniques, in particular by elemental analysis (EA), nitrogen volumetrics (BET), liquid $^1$H nuclear magnetic resonance ($^1$H NMR) and solid $^{31}$P nuclear magnetic resonance ($^{31}$P NMR).

Elemental analysis (EA) can measure, by combustion, the quantity of carbon present on the hybrid organic-inorganic materials. The quantity of phosphorus present on the hybrid organic-inorganic materials is calculated using the molar ratio C/P of the organophosphorus compound.

The term "specific surface area" means the BET specific surface area ($S_{BET}$ in m²/g) determined by nitrogen volumetrics in accordance with American standard ASTM D 3663-78 established from the BRUNAUER-EMMETT-TELLER method described in "The Journal of the American Society", 1938, 60, 309. In the context of this invention, nitrogen adsorption-desorption measurements were carried out at 77K on a Micrometrics Gemini 2360 apparatus using the BET method to calculate the specific surface area. The surface area of the nitrogen molecule is taken to be equal to 13.5 Å² rather than 16.2 Å², the value recommended for metal oxides (Jelinek, L Kovāts E, Langmuir 1994, 10, 4225-4231). The samples were initially degassed for 12 hours at 120° C.

Liquid phase $^1$H NMR spectra were obtained from a Bruker Avance DPX 200 apparatus. The chemical displacements (δ, ppm) were with respect to tetramethylsilane.

The liquid phase $^{31}$P NMR spectra were produced on a Bruker Avance AC 200 apparatus. The solid phase $^{31}$P NMR spectra were produced on a Bruker Avance DPX 300 using magic angle spinning (MAS), high power decoupling (HP-DEC), an angle of inclination of 45° and a pulse delay of 10 seconds. The chemical displacements (δ, ppm) were with respect to $H_3PO_4$ (85% in solution in water).

EXAMPLE 1

(In Accordance with the Invention): Surface Modification of $TiO_2$ by $C_3H_7POCl_2$ 1 gram of $TiO_2$, P25 Degussa ($S_{BET}$=45 m²/g, mixture of anatase (70%) and rutile (30%)), dried at 120° C. under reduced pressure (100 Pa) for 15 h, was added to a solution of 0.37 millimoles of $C_3H_7POCl_2$ (59.6 mg) in 10 ml of dry toluene (<0.02% $H_2O$). After stirring for 3 days at ambient temperature and in the dark, the solid was isolated, washed two times with toluene, two times with acetone, then two times with an acetone/permuted water mixture (⁵⁰/₅₀). The solid was then dried at 120° C. under reduced pressure (100 Pa) for 15 h. elemental analysis showed a carbon content of 0.63% by weight, i.e. 2.4 grafts/nm². $^{31}$P NMR spectroscopic analysis showed the presence of signals between 20 and 40 ppm characteristic of the alkylphosphonate species bonded to the $TiO_2$ surface. No titanium phosphate, phosphonate or phosphinate type phase was detected. Infrared spectroscopy confirmed the presence of alkyl chains ($\sigma_{C-H}$ Vibrations at 2939 and 2880 cm$^{-1}$).

EXAMPLE 2

(In Accordance with the Invention): Surface Modification of $TiO_2$ by $C_{12}H_{25}POCl_2$ 1 gram of $TiO_2$, P25 Degussa ($S_{BET}$=45 m²/g, mixture of anatase (70%) and rutile (30%)), dried at 120° C. under reduced pressure (100 Pa) for 15 h, was added to a solution of 0.37 millimoles of $C_{12}H_{25}POCl_2$ (106.2 mg) in 10 ml of dry toluene (<0.02% $H_2O$). After stirring for 3 days at ambient temperature and in the dark, the solid was isolated, washed two times with toluene, two times with acetone, then two times with an acetone/permuted water mixture (⁵⁰/₅₀). The solid was then dried at 120° C. under reduced pressure (100 Pa) for 15 h. Elemental analysis showed a carbon content of 3.50% by weight, i.e. 3.4 grafts/nm². $^{31}$P NMR spectroscopic analysis showed the presence of signals between 20 and 40 ppm characteristic of the alkylphosphonate species bonded to the $TiO_2$ surface. No titanium phosphate, phosphonate or phosphinate type phase was detected. Infrared spectroscopy confirmed the presence of alkyl chains ($\sigma_{C-H}$ Vibrations at 2922 and 2852 cm$^{-1}$).

EXAMPLE 3

(In Accordance with the Invention): Surface Modification of $TiO_2$ by $C_6H_5POCl_7$ 1 gram of $TiO_2$, P25 Degussa ($S_{BET}$=45 m²/g, mixture of anatase (70%) and rutile (30%)), dried at 120° C. under reduced pressure (100 Pa) for 15 h, was added to a solution of 0.895 millimoles of $C_6H_5POCl_2$ (174.53 mg) in 20 ml of dry toluene (<0.02% $H_2O$). After stirring for 3 days at 80° C. and in the dark, the solid was isolated, washed three times with toluene, then three times with permutated water. The solid was then dried at 60° C. for 15 h. Elemental analysis showed a carbon content of 2.83% by weight, i.e. 5.5 grafts/nm². $^{31}$P NMR spectroscopic analysis showed the presence of signals between 10 and 20 ppm characteristic of the arylphosphonate species bonded to the $TiO_2$ surface. No titanium phosphate, phosphonate or phosphinate type phase was detected. Infrared spectroscopy confirmed the presence of alkyl chains ($\sigma_{C-HArom}$ Vibrations at 3057 cm$^{-1}$).

EXAMPLE 4

(In Accordance with the Invention): Surface Modification of $TiO_2$ by $Cl_2OP(CH_2)_3SO_2Cl$ Synthesis of $Cl_2OP(CH_2)_3SO_2Cl$:
A mixture of 1.02 g (5 mmole) of phosphopropylsulphonic acid ($H_2O_3P$—$C_3H_6$—$SO_3H$) and 3.65 mg (0.05 mmol) of dimethylformamide (catalyst) was added dropwise over 2 hours to 2.68 g (22.5 mmol) of thionyl chloride under reflux (79° C.). Reflux was maintained, with stirring, for 6 days. The medium was then concentrated under reduced pressure. The product was obtained in a purity of close to 100% in the form of a brown oil. NMR characterization of the product provided the following signals:

$Cl_2OP(CH_2)_3SO_2Cl$ $^1$H NMR (δ, pm, $CDCl_3$): 3.9 (m, 2H, P—$CH_2$—$CH_2$—$CH_2$—S), 2.9 (m, 2H, P—$CH_2$—$CH_2$——S), 2.6 (m, 2H, P—$CH_2$—$CH_2$—$CH_2$—S).

$^{31}$P NMR (δ, ppm, $CDCl_3$): 47.2.

2 grams of $TiO_2$, P25 Degussa ($S_{BFT}$=45 m²/g, mixture of anatase (70%) and rutile (30%)), dried at 120° C. under reduced pressure (100 Pa) for 15 h, was added to a solution of 0.74 millimoles of $Cl_2OP(CH_2)_3SO_2Cl$ (192 mg) in 20 ml of dry toluene (<0.02% $H_2O$). After stirring for 3 days at 80° C. and in the dark, the solid was isolated, washed two times with toluene, two times with acetone then two times with an acetone/peunuted water mixture (⁵⁰/₅₀). The solid was then dried at 120° C. under reduced pressure for 15 h. Elemental analysis showed a carbon content of 1.14% by weight, i.e. 4.8 grafts/nm². ³¹P NMR spectroscopic analysis showed the presence of signals between 10 and 40 ppm characteristic of the alkylphosphonate species bonded to the $TiO_2$ surface. No titanium phosphate, phosphonate or phosphinate type phase was detected. Infrared spectroscopy confirmed the presence of alkyl chains ($\sigma_{C-H}$ Vibrations at 2939 and 2880 cm⁻¹).

EXAMPLE 5

(Not in Accordance with the Invention): Surface Modification of $TiO_2$ by $HO_2P(CH_2)_3SO_3H$ In this example, the operating conditions defined in EP-A-1 180 396 were used. In a first step, a phosphonate with formula $Br(CH_2)_3PO_3Et_2$ (I') was prepared using the Arbuzov reaction (March J, Advanced Organic Chemistry, 3rd ed, John Wiley & Sons, New York, 1985, p 848).

P(OEt)₃+Br—(CH₂)₃—Br Br—(CH₂)₃—PO₃Et₂EtBr 1 equivalent of triethylphosphite and 1.5 equivalents of 1,3-dibroM-O-P-Ropane were introduced into a reactor under nitrogen. The reactor was brought to 140° C. and maintained at that temperature for 24 h, with stirring. After distilling under a pressure of 10⁻⁴ bar (10 Pascal) at a mean column bottom temperature of 90° C., diethyl bromopropylphosphonate with formula $Br(CH_2)_3PO_3Et_2$ (I') was obtained in a yield of 60%, in moles with respect to the triethylphosphite introduced. This phosphonate was then functionalized using the procedure below, employing a conventional reaction for replacing the halogen atom by a sulphonate group described in the book by March J, Advanced Organic Chemistry, 3rd edition, John Wiley & Sons, New York, 1985 p 363 to obtain the phosphonate with formula $NaSO_2(CH_2)_3PO_3Et_2$ (II). The last step of this preparation was hydrolysis of the P-OEt bonds to a P-OH bond to obtain the phosphonic acid with formula $HSO_3(CH_2)_3PO_3H_2$ (II').

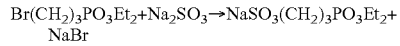
Br(CH₂)₃PO₃Et₂+Na₂SO₃→NaSO₃(CH₂)₃PO₃Et₂+ NaBr

NaSO₃(CH₂)₃PO₃Et₂+2HCl→HSO₃(CH₂)₃PO₃H₂+ 2EtCl 152 mg (0.74 millimoles) of 1-propane-3-phosphonosulphonic acid with formula $HSO_3(CH_2)_3PO_3H_2$ (II') prepared using the procedure described above in a methanol/water mixture (7.5/2.5 ml) was dissolved in a three necked flask. The pH of the solution, measured with a pH meter, which had been calibrated, was 3.1. The pH was then adjusted to 3.5 by adding an aqueous 1N sodium hydroxide solution. A suspension of 2 g (5×10⁻² mole) of $TiO_2$ P25 Degussa (dried overnight at 120° C. under 5 Pa) in 10 ml of permutated water was then added. A coolant was added to the assembly and the reaction mixture was stirred for 3 days at ambient temperature. The solid was filtered and washed 5 times with 50 ml of methanol to remove the physisorbed 1-propane-3-phosphonosulphonic acid. The solid was then washed with permuted water, ethanol, acetone and ether and dried for 5 hours at 120° C. under 5 Pa.

Elemental analysis showed a carbon content of 0.45%, i.e. 1.8 grafts/nm². ³¹P NMR analysis showed the presence of signals between 10 and 20 ppm characteristic of arylphosphonate species bonded to the surface of $TiO_2$. No titanium phosphate, phosphonate or phosphinate type phase was detected. Infrared spectroscopy confirmed the presence of alkyl chains ($\sigma_{C-Harom}$ Vibrations at 3057 cm⁻¹).

The invention claimed is:

1. A grafting process for preparing a hybrid organic-inorganic material (HOIM) with phosphorus-containing bonds between the surface of a solid inorganic substrate containing at least one element M and one or more organic groups, said bonds being of the covalent M-O-P-R type, said process comprising
    a) pretreating solid inorganic substrate, to remove residual water comprising heating said substrate to a temperature in the range of 20° C. to 300° C. at an absolute gas pressure in the range of 0.01 Pa to 0.2 MPa and for a period in the range of 1 to 20 hours,
    b) contacting resultant pretreated inorganic substrate with an anhydrous organic solution of a precursor for said organic group or groups, wherein said precursor is constituted by at least one organophosphorus acid chloride with formula RxP(O)Xy in which x=1or 2, y=3-x, X being chlorine and R designating at least one organic alkyl, aryl or aryl-alkyl group to produce covalent M-O-P-R bonds between the organic and inorganic phases;
    c) filtering and washing the solid obtained in step b);
    d) heat treating the solid obtained in step c) at a temperature in the range 25° C. to 500° C., at an absolute air pressure in the range of 0.01 Pa to 0.2 MPa in which M is selected from groups IB, IIB, IIIB, IVB, VB, VIB, VIIB, VIII, IA, IIA, IIIA, IVA, VA, the lanthanides and actinides of the periodic table, and
    wherein the process avoids the formation of lamellar phases in the surface of the inorganic substrate.

2. The process according to claim 1, in which the organic group or groups are selected from carboxylic acids and their derivatives, amines and their derivatives, sulphonic acids and their derivatives, thiols and their derivatives, and polysulphides and their derivatives.

3. The process according to claim 1, in which said inorganic substrate comprises a single element M.

4. The process according to claim 1, in which said inorganic substrate comprises two to four elements M.

5. The process according to claim 1, in which the inorganic substrate is selected from the group constituted by alumina, titanium dioxide, silica, zeolites and mesostructured silica.

6. The process according to claim 1, in which the inorganic substrate is titanium dioxide.

7. The process according to claim 6, wherein said organophosphorus acid chloride is $C_3H_7POCl_2$.

8. The process according to claim 6, wherein said organophosphorus acid chloride is $C_{12}H_{25}POCl_2$.

9. The process according to claim 6, wherein said organophosphorus acid chloride is $C_6H_5POCl_2$.

10. The process according to claim 6, wherein said organophosphorus acid chloride is $C_{12}OP(CH_2)_3SO_2Cl$.

11. The process according to claim 1, in which the inorganic substrate is selected from iron, aluminium, titanium, silicon, copper, brass and steel.

12. The process according to claim 1, in which the inorganic substrate is selected from carbonates of elements M belonging to said groups IA and IIA.

13. The process according to claim 1, in which the inorganic substrate is selected from talc, apatite, quartz and gypsum.

14. The process according to claim 1, in which the inorganic substrate is selected from silicon nitride, silicon, gallium arsenide, gallium nitride and silicon carbide.

15. A process according to claim 1, wherein the resultant hybrid material has a graft density represented by a phosphorous surface density of 2-10 P atoms/nm².

16. The process according to claim 15, wherein the resultant hybrid organic-inorganic material is free of phosphate, phosphinate and phosphonate phases of elements M, as determined by the absence of peaks associated with said lamellar phases by $^{31}$P NMR analysis.

17. The process according to claim 1, wherein the resultant hybrid material has a graft density represented by a phosphorous surface density of 2-5 P atoms/nm$^2$.

18. The process according to claim 1, wherein the resultant hybrid organic-inorganic material is free of phosphate, phosphinate and phosphonate phases of elements M, as determined by the absence of peaks associated with said lamellar phases by $^{31}$P NMR analysis.

* * * * *